United States Patent [19]

Bundy

[11] 4,144,253

[45] Mar. 13, 1979

[54] 9-DEOXY-9-METHYLENE-PGF-TYPE LACTONES

[75] Inventor: Gordon L. Bundy, Portage, Mich.

[73] Assignee: The Upjohn Company, Kalamazoo, Mich.

[21] Appl. No.: 832,766

[22] Filed: Sep. 12, 1977

Related U.S. Application Data

[60] Division of Ser. No. 682,848, May 4, 1976, Pat. No. 4,060,534, which is a continuation-in-part of Ser. No. 651,622, Jan. 23, 1976, Pat. No. 4,021,467, which is a division of Ser. No. 556,768, Mar. 10, 1975, Pat. No. 3,950,363.

[51] Int. Cl.$^2$ ............................................. C07D 313/00
[52] U.S. Cl. ................................ 260/343.41; 542/413; 542/429
[58] Field of Search .................. 260/343.41; 542/413; 542/429

[56] References Cited

U.S. PATENT DOCUMENTS

| | | | |
|---|---|---|---|
| 4,032,543 | 6/1977 | Bundy | 260/343.41 |
| 4,045,449 | 8/1977 | Bundy | 260/343.41 |

*Primary Examiner*—Natalie Trousof
*Assistant Examiner*—Jane T. Fan
*Attorney, Agent, or Firm*—Robert A. Armitage

[57] ABSTRACT

This invention comprises certain analogs PGE or 11-deoxy-PGE compounds in which the carbonyl at C-9 is replaced by methylene. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

211 Claims, No Drawings

9-DEOXY-9-METHYLENE-PGF-TYPE LACTONES

The present application is a divisional application of Ser. No. 682,848, filed May 4, 1976, now issued as U.S. Pat. No. 4,060,534 on Nov. 29, 1977; which is a continuation-in-part of Ser. No. 651,622 filed Jan. 23, 1976, issued as U.S. Pat. No. 4,021,467 on May 3, 1977; which is a division of Ser. No. 556,768, filed Mar. 10, 1975, issued as U.S. Pat. No. 3,950,363 on Apr. 13, 1976.

The present invention relates to prostaglandin analogs, for which the essential material constituting disclosure therefor is incorporated by reference here from Ser. No. 682,848.

I claim:

1. A prostaglandin of the formula

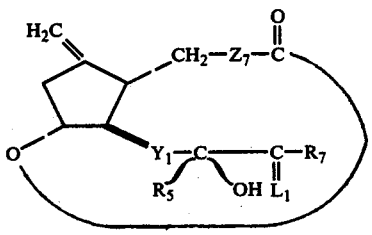

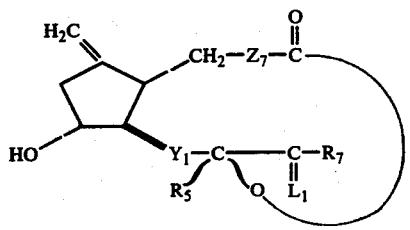

wherein $Y_1$ is trans—CH=CH—, —C≡C—, or —$CH_2CH_2$—, wherein $R_7$ is —$(CH_2)_m$—$CH_3$, wherein m is one to 5, inclusive, or

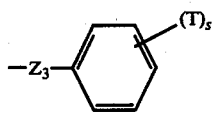

wherein $Z_3$ is oxa or methylene and s is zero, one, 2, or 3 and T is chloro, fluoro, trifluoromethyl, alkyl of one to 3 carbon atoms, inclusive, or alkoxy of one to three carbon atoms, inclusive, with the proviso that not more than two T's are other than alkyl, the various T's being the same or different, and the further proviso that $Z_3$ is oxa only when $R_3$ and $R_4$ are hydrogen or methyl, being the same or different;

wherein $R_5$ is hydrogen or methyl;

wherein $L_1$ is

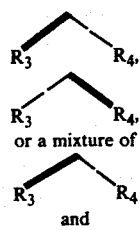

or a mixture of and wherein $R_3$ and $R_4$ are hydrogen, methyl, or fluoro, being the same or different, with the proviso that one of $R_3$ and $R_4$ is fluoro only when the other is hydrogen or fluoro, and wherein $Z_7$ is (1) cis—CH=CH—$CH_2$—$(CH_2)_g$—$CH_2$—,
(2) cis—CH=CH—$CH_2$—$(CH_2)_g$—$CF_2$—,
(3) cis—$CH_2$—CH=CH—$(CH_2)_g$—$CH_2$—,
(4) —$(CH_2)_3$—$(CH_2)_g$—$CH_2$—,
(5) —$(CH_2)_3$—$(CH_2)_g$—$CF_2$—,
(6) —$CH_2$—O—$CH_2$—$(CH_2)_g$—$CH_2$—,
(7) —C≡C—$CH_2$—$(CH_2)_g$—$CH_2$—,
(8) —$CH_2$—C≡C—$(CH_2)_g$—$CH_2$—,

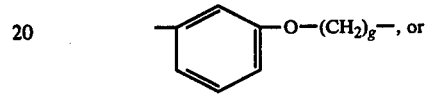

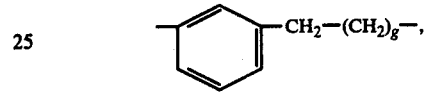

wherein g is one, 2, or 3.

2. A prostaglandin analog according to claim 1, wherein $Y_1$ is —$CH_2CH_2$—.

3. A prostaglandin analog according to claim 2, wherein $Z_7$ is cis—CH=CH—$CH_2$—$(CH_2)_g$—$CF_2$—.

4. 9-Deoxy-9-methylene-2,2-difluoro-13,14-dihydro-$PGF_2$, 1,15-lactone, a prostaglandin analog according to claim 3.

5. A prostaglandin analog according to claim 2, wherein $Z_7$ is —$(CH_2)_3$—$(CH_2)_g$—$CF_2$—.

6. 9-Deoxy-9-methylene-2,2-difluoro-13,14-dihydro-$PGF_1$, 1,15-lactone, a prostaglandin analog according to claim 5.

7. A prostaglandin analog according to claim 2, wherein $Z_7$ is cis—$CH_2$—CH=CH—$(CH_2)_g$—$CH_2$—.

8. 9-Deoxy-9-methylene-cis-4,5-didehydro-13,14-dihydro-$PGF_1$, 1,15-lactone, a prostaglandin analog according to claim 7.

9. A prostaglandin analog according to claim 2, wherein $Z_7$ is —$CH_2$—O—$CH_2$—$(CH_2)_g$—$CH_2$—.

10. 9-Deoxy-9-methylene-5-oxa-13,14-dihydro-$PGF_1$, 1,15-lactone, a prostaglandin analog according to claim 9.

11. A prostaglandin analog according to claim 2, wherein $Z_7$ is —C≡C—$CH_2$—$(CH_2)_g$—$CH_2$—.

12. 9-Deoxy-9-methylene-5,6-didehydro-13,14-dihydro-$PGF_2$, 1,15-lactone, a prostaglandin analog according to claim 11.

13. A prostaglandin analog according to claim 2, wherein $Z_7$ is —$CH_2$—C≡C—$(CH_2)_g$—$CH_2$—.

14. 9-Deoxy-9-methylene-4,4,5,5-tetradehydro-13,14-dihydro-$PGF_1$, 1,15-lactone, a prostaglandin analog according to claim 13.

15. A prostaglandin analog according to claim 2, wherein $Z_7$ is —$(CH_2)_3$—$(CH_2)_g$—$CH_2$—.

16. A prostaglandin analog according to claim 15, wherein $R_5$ is $R_5$.

17. 9-Deoxy-9-methylene-15-epi-13,14-dihydro-$PGF_1$, 1,15-lactone, a prostaglandin analog according to claim 16.

18. A prostaglandin analog according to claim 15, wherein ~R$_5$ is —R$_5$.

19. A prostaglandin analog according to claim 18, wherein m is 3, s is zero or one, and T is chloro, fluoro, or trifluoromethyl.

20. A prostaglandin analog according to claim 19, wherein g is 3.

21. 9-Deoxy-9-methylene-2a,2b-dihomo-15-methyl-13,14-dihydro-PGF$_1$, 1,15-lactone, a prostaglandin analog according to claim 20.

22. 9-Deoxy-9-methylene-2a,2b-dihomo-13,14-dihydro-PGF$_1$, 1,15-lactone, a prostaglandin analog according to claim 20.

23. A prostaglandin analog according to claim 19, wherein g is one.

24. A prostaglandin analog according to claim 23, wherein at least one of R$_3$ and R$_4$ is methyl.

25. A prostaglandin analog according to claim 24, wherein R$_3$ and R$_4$ are both methyl.

26. 9-Deoxy-9-methylene-16,16-dimethyl-13,14-dihydro-PGF$_1$, 1,15-lactone, a prostaglandin analog according to claim 25.

27. A prostaglandin analog according to claim 23, wherein at least one of R$_3$ and R$_4$ is fluoro.

28. A prostaglandin analog according to claim 27, wherein R$_3$ and R$_4$ are both fluoro.

29. 9-Deoxy-9-methylene-16,16-difluoro-13,14-dihydro-PGF$_1$, 1,15-lactone, a prostaglandin analog according to claim 28.

30. A prostaglandin analog according to claim 23, wherein R$_3$ and R$_4$ are both hydrogen.

31. A prostaglandin analog according to claim 30, wherein R$_5$ is methyl.

32. 9-Deoxy-9-methylene-15-methyl-13,14-dihydro-PGF$_1$, 1,15-lactone, a prostaglandin analog according to claim 31.

33. A prostaglandin analog according to claim 30, wherein R$_5$ is hydrogen.

34. 9-Deoxy-9-methylene-13,14-dihydro-PGF$_1$, 1,15-lactone, a prostaglandin analog according to claim 33.

35. A prostaglandin analog according to claim 2, wherein Z$_7$ is cis—CH=CH—CH$_2$—(CH$_2$)$_g$—CH$_2$—.

36. A prostaglandin analog according to claim 35, wherein R$_5$ is R$_5$.

37. A prostaglandin analog according to claim 36, wherein m is 3, s is zero or one, and T is chloro, fluoro, or trifluoromethyl.

38. A prostaglandin analog according to claim 37, wherein g is 3.

39. 9-Deoxy-9-methylene-2a,2b-dihomo-15-epi-15-methyl-13,14-dihydro-PGF$_2$, 1,15-lactone, a prostaglandin analog according to claim 38.

40. 9-Deoxy-9-methylene-2a,2b-dihomo-15-epi-13,14-dihydro-PGF$_2$, 1,15-lactone, a prostaglandin analog according to claim 38.

41. A prostaglandin analog according to claim 37, wherein g is one.

42. A prostaglandin analog according to claim 41, wherein at least one of R$_3$ and R$_4$ is methyl.

43. 9-Deoxy-9-methylene-15-epi-16,16-dimethyl-13,14-dihydro-PGF$_2$, 1,15-lactone, a prostaglandin analog according to claim 42.

44. A prostaglandin analog according to claim 41, wherein at least one of R$_3$ and R$_4$ is fluoro.

45. 9-Deoxy-9-methylene-15-epi-16,16-difluoro-13,14-dihydro-PGF$_2$, 1,15-lactone, a prostaglandin analog according to claim 44.

46. A prostaglandin analog according to claim 41, wherein R$_3$ and R$_4$ are both hydrogen.

47. 9-Deoxy-9-methylene-15-epi-15-methyl-13,14-dihydro-PGF$_2$, 1,15-lactone, a prostaglandin analog according to claim 46.

48. A prostaglandin analog according to claim 35, wherein ~R$_5$ is —R$_5$.

49. A prostaglandin analog according to claim 48, wherein m is 3, s is zero or one, and T is chloro, fluoro, or trifluoromethyl.

50. A prostaglandin analog according to claim 49, wherein g is 3.

51. A prostaglandin analog according to claim 50, wherein at least one of R$_3$ and R$_4$ is methyl.

52. 9-Deoxy-9-methylene-2a,2b-dihomo-16,16-dimethyl-13,14-dihydro-PGF$_2$, 1,15-lactone, a prostaglandin analog according to claim 51.

53. A prostaglandin analog according to claim 50, wherein at least one of R$_3$ is fluoro.

54. 9-Deoxy-9-methylene-2a,2b-dihomo-16,16-difluoro-13,14-dihydro-PGF$_2$, 1,15-lactone, a prostaglandin analog according to claim 53.

55. A prostaglandin analog according to claim 50, wherein R$_3$ and R$_4$ are both hydrogen.

56. 9-Deoxy-9-methylene-2a,2b-dihomo-15-methyl-13,14-dihydro-PGF$_2$, 1,15-lactone, a prostaglandin analog according to claim 55.

57. A prostaglandin analog according to claim 49, wherein g is one.

58. A prostaglandin analog according to claim 57, wherein at least one of R$_3$ and R$_4$ is methyl.

59. A prostaglandin analog according to claim 58, wherein R$_3$ and R$_4$ are both methyl.

60. 9-Deoxy-9-methylene-16,16-dimethyl-13,14-dihydro-PGF$_2$, 1,15-lactone, a prostaglandin analog according to claim 59.

61. A prostaglandin analog according to claim 57, wherein at least one of R$_3$ and R$_4$ is fluoro.

62. A prostaglandin analog according to claim 61, wherein R$_3$ and R$_4$ are both fluoro.

63. A prostaglandin analog according to claim 62, wherein R$_5$ is methyl.

64. 9-Deoxy-9-methylene-15-methyl-16,16-difluoro-13,14-dihydro-PGF$_2$, 1,15-lactone, a prostaglandin analog according to claim 63.

65. A prostaglandin analog according to claim 62, wherein R$_5$ is hydrogen.

66. 9-Deoxy-9-methylene-16,16-difluoro-13,14-dihydro-PGF$_2$, 1,15-lactone, a prostaglandin analog according to claim 65.

67. A prostaglandin analog according to claim 57, wherein R$_3$ and R$_4$ are both hydrogen.

68. A prostaglandin analog according to claim 67, wherein R$_5$ is methyl.

69. 9-Deoxy-9-methylene-15-methyl-13,14-dihydro-PGF$_2$, 1,15-lactone, a prostaglandin analog according to claim 68.

70. A prostaglandin analog according to claim 67, wherein R$_5$ is hydrogen.

71. 9-Deoxy-9-methylene-13,14-dihydro-PGF$_2$, 1,15-lactone, a prostaglandin analog according to claim 70.

72. A prostaglandin analog according to claim 1, wherein Y$_1$ is —C≡C—.

73. A prostaglandin analog according to claim 72, wherein Z$_7$ is cis—CH=CH—CH$_2$—(CH$_2$)$_g$—CF$_2$—.

74. 9-Deoxy-9-methylene-2,2-difluoro-13,14-didehydro-PGF$_2$, 1,15-lactone, a prostaglandin analog according to claim 73.

75. A prostaglandin analog according to claim 72, wherein $Z_7$ is $-(CH_2)_3-(CH_2)_g-CF_2-$.

76. 9-Deoxy-9-methylene-2,2-difluoro-13,14-didehydro-PGF$_1$, 1,15-lactone, a prostaglandin analog according to claim 75.

77. A prostaglandin analog according to claim 72, wherein $Z_7$ is cis-$CH_2-CH=CH-(CH_2)_g-CH_2-$.

78. 9-Deoxy-9-methylene-cis-4,5-didehydro-13,14-didehydro-PGF$_1$, 1,15-lactone, a prostaglandin analog according to claim 77.

79. A prostaglandin analog according to claim 72, wherein $Z_7$ is $-CH_2-O-CH_2-(CH_2)_g-CH_2-$.

80. 9-Deoxy-9-methylene-5-oxa-13,14-didehydro-PGF$_1$, 1,15-lactone, a prostaglandin analog according to claim 79.

81. A prostaglandin analog according to claim 72, wherein $Z_7$ is $-C\equiv C-CH_2-(CH_2)_g-CH_2-$.

82. 9-Deoxy-9-methylene-5,6,13,14-tetradehydro-PGF$_2$, 1,15-lactone, a prostaglandin analog according to claim 81.

83. A prostaglandin analog according to claim 72, wherein $Z_7$ is $-CH_2-C\equiv C-(CH_2)_g-CH_2-$.

84. 9-Deoxy-9-methylene-4,4,5,5,13,14-hexadehydro-PGF$_1$, 1,15-lactone, a prostaglandin according to claim 83.

85. A prostaglandin analog according to claim 72, wherein $Z_7$ is $-(CH_2)_3-(CH_2)_g-CH_2-$.

86. A prostaglandin analog according to claim 85, wherein $\sim R_5$ is $---R_5$.

87. 9-Deoxy-9-methylene-15-epi-13,14-didehydro-PGF$_1$, 1,15-lactone, a prostaglandin analog according to claim 86.

88. A prostaglandin analog according to claim 85, wherein $\sim R_5$ is $---R_5$.

89. A prostaglandin analog according to claim 88, wherein m is 3, s is zero or one, and T is chloro, fluoro, or trifluoromethyl.

90. A prostaglandin analog according to claim 89, wherein g is 3.

91. 9-Deoxy-9-methylene-2a,2b-dihomo-15-methyl-13,14-didehydro-PGF$_1$, 1,15-lactone, a prostaglandin analog according to claim 90.

92. 9-Deoxy-9-methylene-2a,2b-dihomo-13,14-didehydro-PGF$_1$, 1,15-lactone, a prostaglandin analog according to claim 90.

93. A prostaglandin analog according to claim 89, wherein g is one.

94. A prostaglandin analog according to claim 93, wherein at least one of $R_3$ and $R_4$ is methyl.

95. A prostaglandin analog according to claim 94, wherein $R_3$ and $R_4$ are both methyl.

96. 9-Deoxy-9-methylene-16,16-dimethyl-13,14-didehydro-PGF$_1$, 1,15-lactone, a prostaglandin analog according to claim 95.

97. A prostaglandin analog according to claim 93, wherein at least one of $R_3$ and $R_4$ is fluoro.

98. A prostaglandin analog according to claim 97, wherein $R_3$ and $R_4$ are both fluoro.

99. 9-Deoxy-9-methylene-16,16-difluoro-13,14-didehydro-PGF$_1$, 1,15-lactone, a prostaglandin analog according to claim 98.

100. A prostaglandin analog according to claim 93, wherein $R_3$ and $R_4$ are both hydrogen.

101. A prostaglandin analog according to claim 100, wherein $R_5$ is methyl.

102. 9-Deoxy-9-methylene-15-methyl-13,14-didehydro-PGF$_1$, 1,15-lactone, a prostaglandin analog according to claim 101.

103. A prostaglandin analog according to claim 100, wherein $R_5$ is hydrogen.

104. 9-Deoxy-9-methylene-13,14-didehydro-PGF$_1$, 1,15-lactone, a prostaglandin analog according to claim 103.

105. A prostaglandin analog according to claim 72, wherein $Z_7$ is cis-$CH=CH-CH_2-(CH_2)_g-CH_2-$.

106. A prostaglandin analog according to claim 105, wherein $\sim R_5$ is $---R_5$.

107. A prostaglandin analog according to claim 106, wherein m is 3, s is zero or one, and T is chloro, fluoro, or trifluoromethyl.

108. A prostaglandin analog according to claim 107, wherein g is 3.

109. 9-Deoxy-9-methylene-2a,2b-dihomo-15-epi-15-methyl-13,14-didehydro-PGF$_2$, 1,15-lactone, a prostaglandin analog according to claim 108.

110. 9-Deoxy-9-methylene-2a,2b-dihomo-15-epi-13,14-didehydro-PGF$_2$, 1,15-lactone, a prostaglandin analog according to claim 108.

111. A prostaglandin analog according to claim 107, wherein g is one.

112. A prostaglandin analog according to claim 111, wherein at least one of $R_3$ and $R_4$ is methyl.

113. 9-Deoxy-9-methylene-15-epi-16,16-dimethyl-13,14-didehydro-PGF$_2$, 1,15-lactone, a prostaglandin analog according to claim 112.

114. A prostaglandin analog according to claim 111, wherein at least one of $R_3$ and $R_4$ is fluoro.

115. 9-Deoxy-9-methylene-15-epi-16,16-difluoro-13,14-didehydro-PGF$_2$, 1,15-lactone, a prostaglandin analog according to claim 114.

116. A prostaglandin analog according to claim 111, wherein $R_3$ and $R_4$ are both hydrogen.

117. 9-Deoxy-9-methylene-15-epi-15-methyl-13,14-didehydro-PGF$_2$, 1,15-lactone, a prostaglandin analog according to claim 116.

118. A prostaglandin analog according to claim 105, wherein $\sim R_5$ is $-R_5$.

119. A prostaglandin analog according to claim 118, wherein m is 3, s is zero or one, and T is chloro, fluoro, or trifluoromethyl.

120. A prostaglandin analog according to claim 119, wherein g is 3.

121. A prostaglandin analog according to claim 120, wherein at least one of $R_3$ and $R_4$ is methyl.

122. 9-Deoxy-9-methylene-2a,2b-dihomo-16,16-dimethyl-13,14-didehydro-PGF$_2$, 1,15-lactone, a prostaglandin analog according to claim 121.

123. A prostaglandin analog according to claim 120, wherein at least one of $R_3$ and $R_4$ is fluoro.

124. 9-Deoxy-9-methylene-2a,2b-dihomo-16,16-difluoro-13,14-didehydro-PGF$_2$, 1,15-lactone, a prostaglandin analog according to claim 123.

125. A prostaglandin analog according to claim 120, wherein $R_3$ and $R_4$ are both hydrogen.

126. 9-Deoxy-9-methylene-2a,2b-dihomo-15-methyl-13,14-didehydro-PGF$_2$, 1,15-lactone, a prostaglandin analog according to claim 125.

127. A prostaglandin analog according to claim 119, wherein g is one.

128. A prostaglandin analog according to claim 127, wherein at least one of $R_3$ and $R_4$ is methyl.

129. A prostaglandin analog according to claim 128, wherein $R_3$ and $R_4$ are both methyl.

130. 9-Deoxy-9-methylene-16,16-dimethyl-13,14-didehydro-PGF$_2$, 1,15-lactone, a prostaglandin analog according to claim 129.

131. A prostaglandin analog according to claim 127, wherein at least one of R$_3$ and R$_4$ is fluoro.

132. A prostaglandin analog according to claim 131, wherein R$_3$ and R$_4$ are both fluoro.

133. A prostaglandin analog according to claim 132, wherein R$_5$ is methyl.

134. 9-Deoxy-9-methylene-15-methyl-16,16-difluoro-13,14-didehydro-PGF$_2$, 1,15-lactone, a prostaglandin analog according to claim 133.

135. A prostaglandin analog according to claim 132, wherein R$_5$ is hydrogen.

136. 9-Deoxy-9-methylene-16,16-difluoro-13,14-didehydro-PGF$_2$, 1,15-lactone, a prostaglandin analog according to claim 135.

137. A prostaglandin analog according to claim 127, wherein R$_3$ and R$_4$ are both hydrogen.

138. A prostaglandin analog according to claim 137, wherein R$_5$ is methyl.

139. 9-Deoxy-9-methylene-15-methyl-13,14-didehydro-PGF$_2$, 1,15-lactone, a prostaglandin analog according to claim 138.

140. A prostaglandin analog according to claim 137, wherein R$_5$ is hydrogen.

141. 9-Deoxy-9-methylene-13,14-didehydro-PGF$_2$, 1,15-lactone, a prostaglandin analog according to claim 140.

142. A prostaglandin analog according to claim 1, wherein Y$_1$ is trans—CH=CH—.

143. A prostaglandin analog according to claim 142, wherein Z$_7$ is cis—CH=CH—CH$_2$—(CH$_2$)$_g$—CF$_2$—.

144. 9-Deoxy-9-methylene-2,2-difluoro-PGF$_2$, 1,15-lactone, a prostaglandin analog according to claim 143.

145. A prostaglandin analog according to claim 142, wherein Z$_7$ is —(CH$_2$)$_3$—(CH$_2$)$_g$—CF$_2$—.

146. 9-Deoxy-9-methylene-2,2-difluoro-PGF$_1$, 1,15-lactone, a prostaglandin analog according to claim 145.

147. A prostaglandin analog according to claim 142, wherein Z$_7$ is cis—CH$_2$—CH=CH—(CH$_2$)$_g$—CH$_2$—.

148. 9-Deoxy-9-methylene-cis-4,5-didehydro-PGF$_1$, 1,15-lactone, a prostaglandin analog according to claim 147.

149. A prostaglandin analog according to claim 142, wherein Z$_7$ is —CH$_2$—O—CH$_2$—(CH$_2$)$_g$—CH$_2$—.

150. 9-Deoxy-9-methylene-5-oxa-PGF$_1$, 1,15-lactone, a prostaglandin analog according to claim 149.

151. A prostaglandin analog according to claim 142, wherein Z$_7$ is —C≡C—CH$_2$—(CH$_2$)$_g$—CH$_2$—.

152. 9-Deoxy-9-methylene-5,6-didehydro-PGF$_2$, 1,15-lactone, a prostaglandin analog according to claim 151.

153. A prostaglandin analog according to claim 142, wherein Z$_7$ is —CH$_2$—C≡C—(CH$_2$)$_g$—CH$_2$—.

154. 9-Deoxy-9-methylene-4,4,5,5-tetradehydro-PGF$_1$, 1,15-lactone, a prostaglandin analog according to claim 153.

155. A prostaglandin analog according to claim 142, wherein Z$_7$ is —(CH$_2$)$_3$—(CH$_2$)$_g$—CH$_2$—.

156. A prostaglandin analog according to claim 155, wherein ~ R$_5$ is — R$_5$.

157. 9-Deoxy-9-methylene-15-epi-PGF$_1$, 1,15-lactone, a prostaglandin analog according to claim 156.

158. A prostaglandin analog according to claim 155, wherein ~ R$_5$ is — R$_5$.

159. A prostaglandin analog according to claim 158, wherein m is 3, s is zero or one, and T is chloro, fluoro, or trifluoromethyl.

160. A prostaglandin analog according to claim 159, wherein g is 3.

161. 9-Deoxy-9-methylene-2a,2b-dihomo-15-methyl-PGF$_1$, 1,15-lactone, a prostaglandin analog according to claim 160.

162. 9-Deoxy-9-methylene-2a,2b-dihomo-PGF$_1$, 1,15-lactone, a prostaglandin analog according to claim 160.

163. A prostaglandin analog according to claim 159, wherein g is one.

164. A prostaglandin analog according to claim 163, wherein at least one of R$_3$ and R$_4$ is methyl.

165. A prostaglandin analog according to claim 164, wherein R$_3$ and R$_4$ are both methyl.

166. 9-Deoxy-9-methylene-16,16-dimethyl-PGF$_1$, 1,15-lactone, a prostaglandin analog according to claim 165.

167. A prostaglandin analog according to claim 163, wherein at least one of R$_3$ and R$_4$ is fluoro.

168. A prostaglandin analog according to claim 167, wherein R$_3$ and R$_4$ are both fluoro.

169. 9-Deoxy-9-methylene-16,16-difluoro-PGF$_1$, 1,15-lactone, a prostaglandin analog according to claim 168.

170. A prostaglandin analog according to claim 163, wherein R$_3$ and R$_4$ are both hydrogen.

171. A prostaglandin analog according to claim 170, wherein R$_5$ is methyl.

172. 9-Deoxy-9-methylene-15-methyl-PGF$_1$, 1,15-lactone, a prostaglandin analog according to claim 171.

173. A prostaglandin analog according to claim 170, wherein R$_5$ is hydrogen.

174. 9-Deoxy-9-methylene-PGF$_1$, 1,15-lactone, a prostaglandin analog according to claim 173.

175. A prostaglandin analog according to claim 142, wherein Z$_7$ is cis—CH=CH—CH—CH$_2$—(CH$_2$)$_g$—CH$_2$—.

176. A prostaglandin analog according to claim 175, wherein ~ R$_5$ is — R$_5$.

177. A prostaglandin analog according to claim 176, wherein m is 3, s is zero or one, and T is chloro, fluoro, or trifluoromethyl.

178. A prostaglandin analog according to claim 177, wherein g is 3.

179. 9-Deoxy-9-methylene-2a,2b-dihomo-15-epi-15-methyl-PGF$_2$, 1,15-lactone, a prostaglandin analog according to claim 178.

180. 9-Deoxy-9-methylene-2a,2b-dihomo-15-epi-PGF$_2$, 1,15-lactone, a prostaglandin analog according to claim 178.

181. A prostaglandin analog according to claim 177, wherein g is one.

182. A prostaglandin analog according to claim 181, wherein at least one of R$_3$ and R$_4$ is methyl.

183. 9-Deoxy-9-methylene-15-epi-16,16-dimethyl-PGF$_2$, 1,15-lactone, a prostaglandin analog according to claim 182.

184. A prostaglandin analog according to claim 181, wherein at least one of R$_3$ and R$_4$ is fluoro.

185. 9-Deoxy-9-methylene-15-epi-16,16-difluoro-PGF$_2$, 1,15-lactone, a prostaglandin analog according to claim 184.

186. A prostaglandin analog according to claim 181, wherein R$_3$ and R$_4$ are both hydrogen.

187. 9-Deoxy-9-methylene-15-epi-15-methyl-$PGF_2$, 1,15-lactone, a prostaglandin analog according to claim 186.

188. A prostaglandin analog according to claim 175, wherein $\sim R_5$ is $— R_5$.

189. A prostaglandin analog according to claim 188, wherein m is 3, s is zero or one, and T is chloro, fluoro, or trifluoromethyl.

190. A prostaglandin analog according to claim 189, wherein g is 3.

191. A prostaglandin analog according to claim 190, wherein at least one of $R_3$ and $R_4$ is methyl.

192. 9-Deoxy-9-methylene-2a,2b-dihomo-16,16-dimethyl-$PGF_2$, 1,15-lactone, a prostaglandin analog according to claim 191.

193. A prostaglandin analog according to claim 190, wherein at least one of $R_3$ and $R_4$ is fluoro.

194. 9-Deoxy-9-methylene-2a,2b-dihomo-16,16-difluoro-$PGF_2$, 1,15-lactone, a prostaglandin analog according to claim 193.

195. A prostaglandin analog according to claim 190, wherein $R_3$ and $R_4$ are both hydrogen.

196. 9-Deoxy-9-methylene-2a,2b-dihomo-15-methyl-$PGF_2$, 1,15-lactone, a prostaglandin analog according to claim 195.

197. A prostaglandin analog according to claim 189, wherein g is one.

198. A prostaglandin analog according to claim 197, wherein at least one of $R_3$ and $R_4$ is methyl.

199. A prostaglandin analog according to claim 198, wherein $R_3$ and $R_4$ are both methyl.

200. 9-Deoxy-9-methylene-16,16-dimethyl-$PGF_2$, 1,15-lactone, a prostaglandin analog according to claim 199.

201. A prostaglandin analog according to claim 197, wherein at least one of $R_3$ and $R_4$ is fluoro.

202. A prostaglandin analog according to claim 201, wherein $R_3$ and $R_4$ are both fluoro.

203. A prostaglandin analog according to claim 202, wherein $R_5$ is methyl.

204. 9-Deoxy-9-methylene-15-methyl-16,16-difluoro-$PGF_2$, 1,15-lactone, a prostaglandin analog according to claim 203.

205. A prostaglandin analog according to claim 202, wherein $R_5$ is hydrogen.

206. 9-Deoxy-9-methylene-16,16-difluoro-$PGF_2$, 1,15-lactone, a prostaglandin analog according to claim 205.

207. A prostaglandin analog according to claim 197, wherein $R_3$ and $R_4$ are both hydrogen.

208. A prostaglandin analog according to claim 207, wherein $R_5$ is methyl.

209. 9-Deoxy-9-methylene-15-methyl-$PGF_2$, 1,15-lactone, a prostaglandin analog according to claim 208.

210. A prostaglandin analog according to claim 207, wherein $R_5$ is hydrogen.

211. 9-Deoxy-9-methylene-$PGF_2$, 1,15-lactone, a prostaglandin analog according to claim 210.

* * * * *

UNITED STATES PATENT OFFICE
CERTIFICATE OF CORRECTION

Patent No. 4,144,253            Dated March 13, 1979

Inventor(s) Gordon L. Bundy

It is certified that error appears in the above-identified patent and that said Letters Patent are hereby corrected as shown below:

Column 1, line 28, and -- or -- should appear between the two formulae;

Column 2, line 58, "-C=C-" should read -- -C≡C- --; line 65, "wherein $R_5$ is    $R_5$ -- should read -- wherein $\sim\!R_5$ is $--R_5$;

Column 3, line 2, "wherein    $R_5$ is" should read -- wherein $\sim\!R_5$ is --; line 45, "wherein    $R_5$ is    $R_5$" should read -- wherein $\sim\!R_5$ is $--R_5$ --;

Column 4, line 19, "$R_3$ is fluoro" should read -- $R_3$ and $R_4$ is fluoro --.

Signed and Sealed this

*Eleventh* Day of *September 1979*

[SEAL]

*Attest:*

LUTRELLE F. PARKER

*Attesting Officer*       *Acting Commissioner of Patents and Trademarks*